US010222318B2

(12) United States Patent
Faez et al.

(10) Patent No.: US 10,222,318 B2
(45) Date of Patent: Mar. 5, 2019

(54) PARTICLE DETECTION APPARATUS

(71) Applicants: Universiteit Leiden, Leiden (NL); Max-Planck-Gesellschaft zur Foerderung der Wissenschaften e.V., Munich (DE)

(72) Inventors: Sanli Ebrahimi Pour Faez, Utrecht (NL); Vahid Sandoghdar, Erlangen (DE)

(73) Assignees: UNIVERSITEIT LEIDEN, Leiden (NL); MAX-PLANCK-GESELLSCHAFT ZUR FOERDERUNG DER WISENSCHAFTEN E.V., Muenchen (DK)

( * ) Notice: Subject to any disclaimer, the term of this patent is extended or adjusted under 35 U.S.C. 154(b) by 61 days.

(21) Appl. No.: 15/510,104

(22) PCT Filed: Sep. 9, 2015

(86) PCT No.: PCT/EP2015/070647
§ 371 (c)(1),
(2) Date: Mar. 9, 2017

(87) PCT Pub. No.: WO2016/038108
PCT Pub. Date: Mar. 17, 2016

(65) Prior Publication Data
US 2017/0254739 A1    Sep. 7, 2017

(30) Foreign Application Priority Data

Sep. 9, 2014   (GB) .................................. 1415919.8

(51) Int. Cl.
*G01N 15/14* (2006.01)
*G01N 21/53* (2006.01)
(Continued)

(52) U.S. Cl.
CPC ...... *G01N 15/1436* (2013.01); *G01N 15/1459* (2013.01); *G01N 15/1484* (2013.01);
(Continued)

(58) Field of Classification Search
CPC ........... G01N 15/1436; G01N 15/1459; G01N 15/1484; G01N 2015/0038;
(Continued)

(56) References Cited

U.S. PATENT DOCUMENTS

| 5,175,596 A | 12/1992 | Dick et al. |
| 2004/0018611 A1* | 1/2004 | Ward ................ B01L 3/502761 435/287.2 |

(Continued)

FOREIGN PATENT DOCUMENTS

| EP | 1 801 560 A1 | 6/2007 |
| GB | 2027547 A | 2/1980 |
| GB | 2419406 A | 4/2006 |

OTHER PUBLICATIONS

International Search Report for corresponding patent application No. PCT/EP2015/070647 dated Nov. 25, 2015.
(Continued)

*Primary Examiner* — Mark R Gaworecki
(74) *Attorney, Agent, or Firm* — Renner, Otto, Boisselle & Sklar, LLP

(57) ABSTRACT

There is provided a particle detection apparatus (30) comprising:
 a channel (32) including an inlet and at least one channel wall, the inlet permitting light to be introduced into the channel (32), the or each channel wall being arranged to define a channel path through which light may propagate;
 a light source (34) configured to introduce light into the channel (32) via the inlet, the channel (32) being
(Continued)

shaped to guide the light to propagate along the channel path for illuminating a particle or a plurality of particles located in the channel path; and a monitoring device (36) configured to detect scattered light that is created by the illumination of the or each particle by the guided light and that leaves the channel (32) by passing through the or each channel wall.

29 Claims, 8 Drawing Sheets

(51) Int. Cl.
*G01N 21/47* (2006.01)
*G01N 21/64* (2006.01)
*B01L 3/00* (2006.01)
*G01N 15/00* (2006.01)

(52) U.S. Cl.
CPC ........... *G01N 21/474* (2013.01); *G01N 21/53* (2013.01); *G01N 21/6458* (2013.01); *B01L 3/502761* (2013.01); *G01N 2015/0038* (2013.01); *G01N 2021/4742* (2013.01); *G01N 2201/08* (2013.01)

(58) Field of Classification Search
CPC ......... G01N 2021/4742; G01N 21/474; G01N 21/53; G01N 21/6458; G01N 2201/08
See application file for complete search history.

(56) References Cited

U.S. PATENT DOCUMENTS

| 2009/0161108 | A1 | 6/2009 | Frese et al. | |
| 2009/0245718 | A1 | 10/2009 | Li et al. | |
| 2010/0142054 | A1* | 6/2010 | Kastrup | G01N 21/6458 359/579 |

OTHER PUBLICATIONS

Li-Li Huang and Hai-Yan Xie, Progress on the labeling and single-particle tracking technologies of viruses, Analyst, Mar. 20, 2014, 3336-3346, Issue 13, Royal Society of Chemistry.

Frank Vollmer et al, Whispering-gallery-mode biosensing: label-free detection down to single molecules, Nature Methods 5, 591-596 (2008).

Philipp Kukura et al, High-speed nanoscopic tracking of the position and orientation of a single virus, Nature Methods 6, 923-927 (2009).

Allen H. J. Yang et al, Optical manipulation of nanoparticles and biomolecules in sub-wavelength slot waveguides, Nature 457, 71-75 (Jan. 1, 2009).

M. K. Garbos et al, Doppler velocimetry on microparticles trapped and propelled by laser light in liquid-filled photonic crystal fiber, vol. 36, Issue 11, pp. 2020-2022 (2011).

E. Van Der Pol et al, Particle size distribution of exosomes and microvesicles determined by transmission electron microscopy, flow cytometry, nanoparticle tracking analysis, and resistive pulse sensing, Journal of Thrombosis and Haemotosis, vol. 12, Issue 7, Jul. 2014, pp. 1182-1192.

Holger Schmidt et al, The photonic integration of non-solid media using optofluidics, Nature Photonics 5, 598-604 (2011).

Sanli Faez et al, Fast, label-free tracking of single viruses and weakly scattering nanoparticles in a nano-fluidic optical fiber, https://arxiv.org/abs/1506.06500v1, Version 1 submitted on Jun. 22, 2015.

Sanli Faez et al, Fast, label-free tracking of single viruses and weakly scattering nanoparticles in a nano-fluidic optical fiber, https://arxiv.org/abs/1506.06500v2, Version 2 submitted on Jul. 18, 2015.

Sanli Faez et al, Opto-fluidic tracking of Rayleigh particles with elastic light scattering, Focus on Optical Microscopy, Veldhoven, Netherlands, Jan. 20, 2015.

* cited by examiner

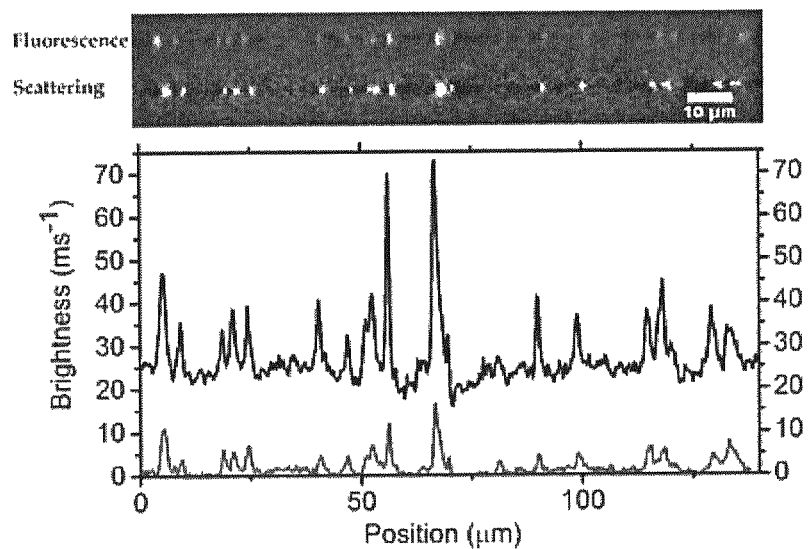
Figure 9
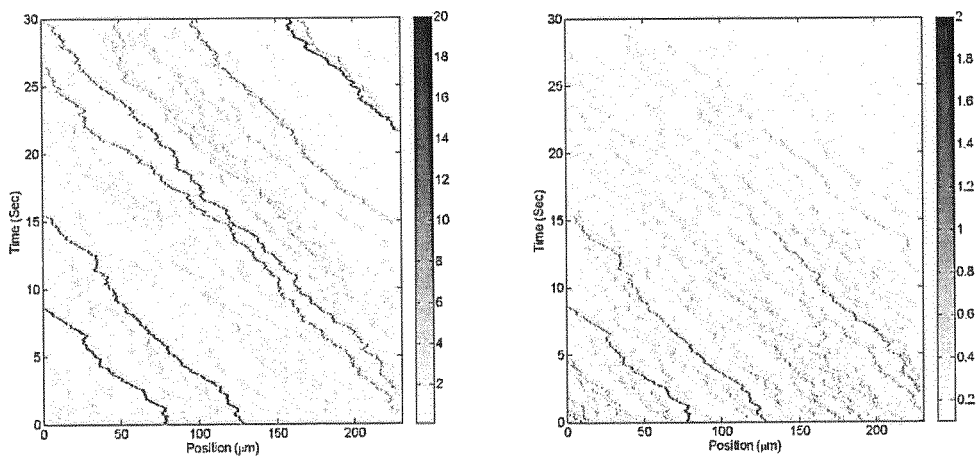
Figure 10
Figure 11

PARTICLE DETECTION APPARATUS

This application is a national phase of International Application No. PCT/EP2015/070647 filed Sep. 9, 2015 and published in the English language.

This invention relates to a particle detection apparatus.

It is known to use various microscopy techniques to detect and study the behaviour of nanoparticles at the nanoscale. Examples of such microscopy techniques include electron microscopy and fluorescent microscopy.

According to a first aspect of the invention, there is provided a particle detection apparatus comprising:

- a channel including an inlet and at least one channel wall, the inlet permitting light to be introduced into the channel, the or each channel wall being arranged to define a channel path through which light may propagate;
- a light source configured to introduce light into the channel via the inlet, the channel being shaped to guide the light to propagate along the channel path for illuminating a particle or a plurality of particles located in the channel path; and
- a monitoring device configured to detect scattered light that is created by the illumination of the or each particle by the guided light and that leaves the channel by passing through the or each channel wall.

In a preferred embodiment of the invention the inlet may be configured as an open inlet.

The inlet being an open inlet allows the light source to directly introduce light into the channel via the open inlet, i.e. the light enters the channel without passing through an intermediate object such as a channel wall.

Such an open inlet may be configured to permit the or each particle to be introduced into the channel.

In further embodiments of the invention the inlet may be configured as a light incoupling inlet.

The particle detection apparatus of the invention permits optical detection of particles that are freely diffusing in a fluid (e.g. liquid or gas) present in the channel path. In particular, the configuration of the particle detection apparatus of the invention permits use of coherent and/or incoherent light scattering to detect very small particles, especially those in the sub-100 nm range.

By configuring the channel and monitoring device in the manner set out above, any light that is not scattered by the or each particle stays guided along the channel path so that only the scattered light is detected by the monitoring device. This may be achieved by, for example, the scattered light leaving the channel through the or each channel wall at a non-zero angle to a guided direction of the guided light. This in turn provides excellent signal to background and signal to noise ratios and thereby enhances the detection of the or each particle, thus preventing the detected scattered light from being overwhelmed by direct detection of the residual scattering of the illuminating guided light.

In addition the configuration of the particle detection apparatus of the invention allows the or each particle in the channel path to stay illuminated by the guided light and thereby remain in the imaging plane and not diffuse out of focus. Keeping the or each particle in the illumination plane of the guide light not only obviates the need for immobilisation of particles in a restricted volume, such as that performed in cryogenic electron microscopy, and thereby results in a less complex and cheaper particle detection apparatus, but also provides a prolonged detection period that permits enhanced real-time tracking of the or each particle and increases the obtainable amount of information about the or each particle.

Furthermore the configuration of the particle detection apparatus of the invention enables coherent illumination of a plurality of particles so that, when the plurality of particles approach each other, any resultant near-field interference effect results in enhancement of the detection sensitivity of the particle detection apparatus of the invention.

The improved detection capabilities of the particle detection apparatus of the invention as set out above not only obviates the need for a specialised monitoring device to detect the or each particle and thereby permits use of simpler and cheaper monitoring devices, such as an optical microscope, a smartphone camera or simpler photo-detection electronics, but also permits detection of the or each particle under ambient conditions, instead of specific conditions as required by cryogenic electron microscopy.

The monitoring device may be configured to detect the scattered light to study the or each particle in different ways, examples of which are as follows.

The monitoring device may be configured to measure the coherent scattering intensity of the scattered light, the incoherent scattering intensity of the scattered light, the spectrum of the scattered light, the distribution of the scattered light over a plurality of directions and/or the dynamic motion of one or more particles, preferably the Einstein-Stokes diffusion constant of the or each particle.

Measurement of the scattering intensity of the scattered light permits the study of particle interaction. For example, measurement of the scattering intensity of the scattered light permits the study of particle binding and unbinding events through detection of quadratic changes in the scattering intensity, the spectral response or the diffusion constant of the or each particle.

In addition the simultaneous measurement of the scattering intensity and the Einstein-Stokes diffusion constant of the or each particle allows an aggregate of particles to be distinguished from a single larger particle even if they both exhibit similar scattering intensities.

The monitoring device may be configured to track the or each particle's motion through detection of the scattered light. Such tracking of the or each particle's motion permits the study of the hydrodynamic behaviour of the or each particle.

The monitoring device may be configured to measure an emission spectrum of the or each particle. This permits identification of the or each particle on the basis of its spectral features.

The monitoring device may be configured to detect fluorescent light that is created by the illumination of the or each particle by the guided light and that leaves the channel by passing through the or each channel wall.

The monitoring device may be configured to detect coherently scattered light and/or incoherently scattered light, and optionally detect the spectrum of the coherently scattered light and/or incoherently scattered light, that is created by the illumination of the or each particle by the guided light and that leaves the channel by passing through the or each channel wall.

Optionally the monitoring device may be configured to track the or each particle's motion through detection of the coherently scattered light and/or incoherently scattered light.

The configuration of the monitoring device to detect scattered light permits the use of metallic, semiconductor or organic contrast agents to enhance the polarizability of the or each particle and thereby enhance the detection sensitivity of the particle detection apparatus.

Moreover the configuration of the monitoring device to detect both scattered and fluorescent light permits simultaneous measurement of the scattering and fluorescence in order to, for example, count the number of fluorescent particles via stepwise bleaching, or to measure an emission spectrum of the or each particle to identify the or each particle on the basis of its spectral features.

The choice of channel used in the particle detection apparatus of the invention may vary depending on a range of factors, such as particle size, chemical composition, equipment availability and so on.

The size of the channel may vary depending on the size of the or each particle to be detected. For example, the or each channel wall may enclose a sub-wavelength bore that defines the channel through which light may propagate, and/or the channel may be arranged to convey at least one particle that is smaller than the wavelength of the guided light.

The channel may be formed in different ways to enable detection of the size of the or each particle to be detected. The channel may be formed in or as
  a waveguide;
  a chip-based platform, optionally a lithographically formed chip-based platform; or
  a capillary.

The channel may be formed in or as an optical fibre. The optical fibre may be a single-mode optical fibre. The use of such an optical fibre improves the manner in which the light is guided along the channel path, and thereby improves the resultant illumination of the or each particle located in the channel path and the subsequent scattering of light.

The material of the optical fibre may vary. For example, the optical fibre may be made from silica or polymer.

The particle detection apparatus may include a driving mechanism for driving the or each particle to flow along the channel path. In one example of such a driving mechanism, electrodes may be incorporated into the channel to permit use of an electrophoretic force to steer the or each particle along the channel path. In another example of such a driving mechanism, the driving mechanism may be external to the channel and may be configured to generate an electric field so as to provide an electrophoretic force to steer the or each particle along the channel path.

Optionally the driving mechanism may be configured to drive the or each particle to overcome its or their thermal Brownian motion when driving the or each particle to flow along the channel path. The remote manipulation of the or each particle in a manner that is strong and fast enough to overcome its or their thermal Brownian motion is made possible by the availability of active feedback provided through the use of the particle detection apparatus to track the motion of the or each particle.

The monitoring device may include at least one light detector and/or an imaging device configured to process the detected light so as to create an output signal corresponding to the or each particle. The output signal may be static or dynamic. The creation of the output signal permits visualisation of the or each particle.

The particle detection apparatus may include a plurality of channels, each channel including an inlet and at least one channel wall, each inlet permitting light to be introduced into the respective channel, the or each channel wall being arranged to define a respective channel path through which light may propagate. Optionally the monitoring device may be configured to simultaneously detect scattered light that is created by the illumination of the or each particle by the guided light and that leaves each channel by passing through the or each corresponding channel wall.

The particle detection apparatus may include a plurality of light sources, the plurality of light sources being configured to introduce light into the channel via the inlet. Optionally the plurality of light sources may be configured to simultaneously introduce light into the channel via the inlet.

The particle detection apparatus may include a plurality of monitoring devices, the plurality of monitoring devices being configured to detect scattered light that is created by the illumination of the or each particle by the guided light and that leaves the channel by passing through the or each channel wall. Optionally the plurality of monitoring devices may be configured to simultaneously detect scattered light that is created by the illumination of the or each particle by the guided light and that leaves the channel by passing through the or each channel wall.

According to a second aspect of the invention, there is provided a method of detecting at least one particle, the method comprising the steps of:
  providing a channel including an inlet and at least one channel wall, the inlet permitting light to be introduced into the channel, the or each channel wall being arranged to define a channel path through which light may propagate;
  providing a particle or a plurality of particles in the channel path;
  introducing light into the channel via the inlet, the channel being shaped to guide the light along the channel path and thereby illuminate the particle or the plurality of particles located in the channel path; and
  detecting scattered light that is created by the illumination of the or each particle by the guided light and that leaves the channel by passing through the or each channel wall.

It will be understood that the features of the particle detection apparatus according to the first aspect of the invention applies mutatis mutandis to the method of detecting at least one particle according to the second aspect of the invention. It follows that the corresponding advantages described above with reference to the first aspect of the invention applies mutatis mutandis to the second aspect of the invention.

A preferred embodiment of the invention will now be described, by way of a non-limiting example, with reference to the accompanying drawings in which:

FIGS. 9 to 11 illustrate the simultaneous tracking of fluorescence and scattered light from dielectric latex nanoparticles using the particle detection apparatus of FIG. 1;

Figure 1:
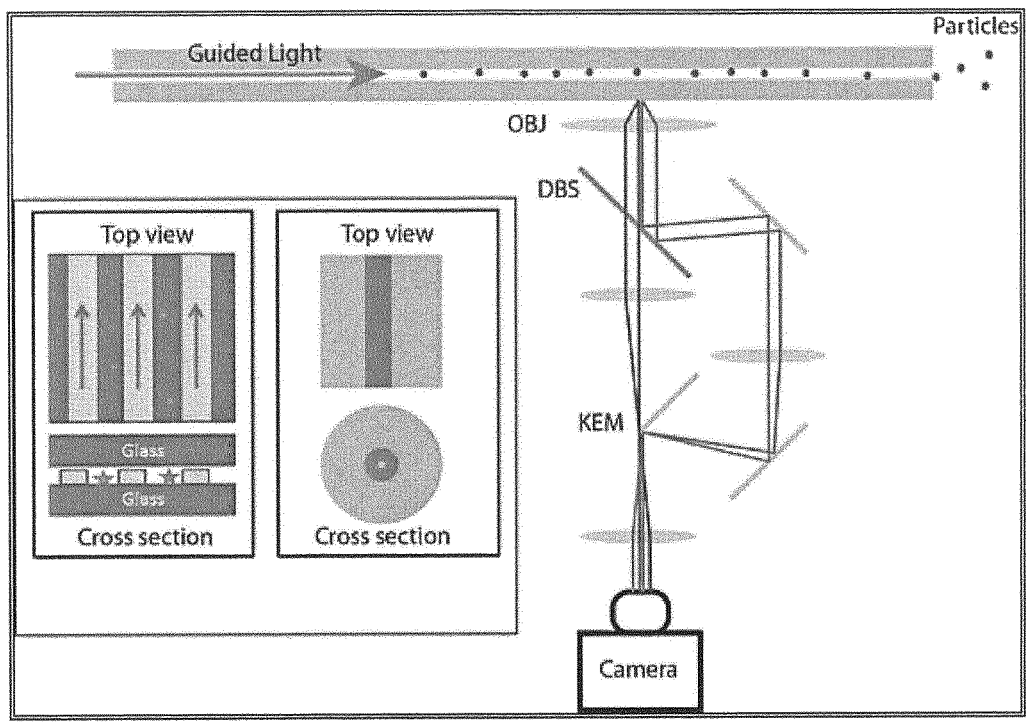
FIG. 1 shows schematically a particle detection apparatus according to an embodiment of the invention.

A particle detection apparatus according to an embodiment of the invention is shown in FIG. 1 and is designated generally by the reference numeral 30.

The particle detection apparatus 30 comprises a channel 32, a light source 34 and a monitoring device 36.

Figure 2:
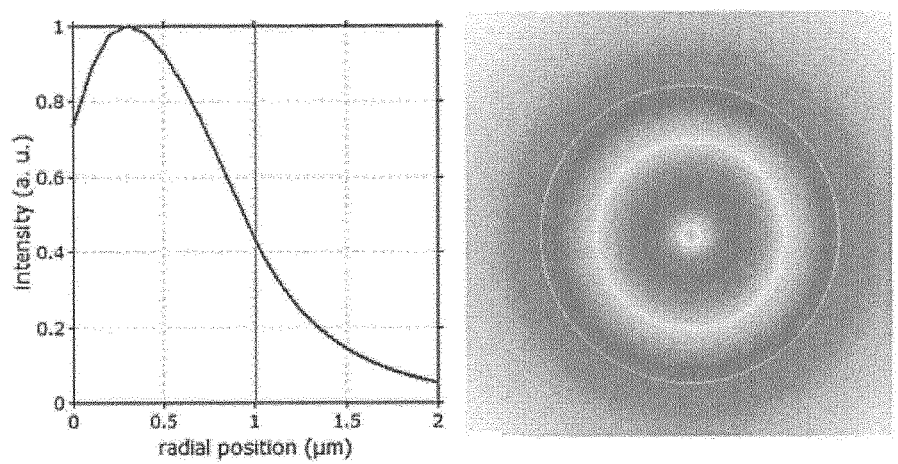
FIG. 2 shows the light intensity profile in an optical fibre that forms part of the particle detection apparatus of FIG. 1.

The channel 32 is formed in a single-mode, optical fibre 38 that is made from silica and includes a sub-wavelength bore. The channel 32 includes an inlet and a channel wall. The inlet permits light to be introduced into the channel 32. The channel wall encloses a 200 nm tubular bore that defines a channel path through which light may propagate. FIG. 2 shows a mode profile of the optical fibre 38 at 670 nm.

The optical fibre 38 may instead be made from polymer. In other embodiments of the invention, the channel 32 is formed as a waveguide 40 fabricated on a chip-based platform by way of lithography, as shown in FIG. 1, or as a capillary.

In use, a plurality of particles is conveyed along the channel path by way of a capillary force or by application of an external pressure.

The light source 34 is configured to introduce light into the channel 32 via the inlet. In the embodiment shown, the light source 34 is a laser. In use, the tubular shape of the channel 32 guides the light to propagate in a single mode along the channel path and thereby illuminate each particle located in the channel path.

The monitoring device 36 includes an objective OBJ, which is configured to result in an overall magnification of 400× and an effective field of view of more than 200 μm, a dichromatic beam splitter DBS, a knife-edge mirror KEM, and a scientific complementary metal-oxide-semiconductor (sCMOS) camera with a maximum frame rate of 3.5 kHz for a 6 pixels by 1024 pixels area. The objective OBJ is positioned outside the channel wall to collect light that leaves the channel 32 by passing through the channel wall. The dichromatic beam splitter DBS and knife-edge mirror KEM are positioned between the objective OBJ and the sCMOS camera such that the dichromatic beam splitter DBS separates fluorescent light from the light collected by the objective OBJ and the knife-edge mirror KEM subsequently combines the fluorescent light and the remainder of the light collected by the objective OBJ prior to their simultaneous imaging by the sCMOS camera. In this manner the monitoring device 36 is configured to detect light that is created by the illumination of each particle by the guided light and that leaves the channel 32 by passing through the channel wall.

The imaged area may be immersed in index-matching oil to overcome aberrations caused by the outer cylindrical shape of the optical fibre 38. Alternatively the optical fibre's cladding may be index-matched to a flat glass slide to obtain an almost isotropic point-like imaging of the particles on the sCMOS camera.

Use of the particle detection apparatus 30 to detect one or more particles is described as follows.

Initially the particles to be conveyed along the channel path is labelled with fluorophores. After the particles to be conveyed along the channel path are introduced into the channel 32, the particles freely diffuse in a fluid (e.g. liquid or gas) present in the channel path.

During the conveyance of the particles along the channel path, light is introduced into the channel 32 via the inlet to illuminate each particle located in the channel path. Due to the confinement of the guided light in the channel 32 and the sub-wavelength dimension of the bore of the channel 32, the illumination of each particle results in scattering due to the polarizability and size of the particles and fluorescence due to the presence of the fluorophores. When the size of a particle is smaller than the wavelength of the guided light, illumination of that particle results in coherent and/or incoherent light scattering.

Part of the resultant scattered light and fluorescent light leave the channel 32 through the channel wall at a non-zero angle to a guided direction of the guided light. The objective collects the scattered light and fluorescent light, which is then transmitted to the sCMOS camera for imaging. The sCMOS camera subsequently processes the detected light so as to create an output image of each illuminated particle to thereby permit visualisation of each illuminated particle.

Meanwhile any light that is not scattered by the particles stays guided along the channel path. This results in excellent signal to background and signal to noise ratios and thereby enhances the detection of each illuminated particle, thus preventing the detected scattered light from being overwhelmed by direct detection of the residual scattering of the illuminating guided light.

Detection of the scattered light and fluorescent light by the particle detection apparatus 30 permits study of each particle in different ways, examples of which are as follows.

The configuration of the particle detection apparatus 30 permit use of the effects of coherent and/or incoherent light scattering to detect very small particles, especially those in the sub-100 nm range.

Figure 3:
FIGS. 3 to 5 illustrate the scattering intensity as a function of position when an aqueous suspension of dielectric latex nanoparticles are conveyed along a channel path of the particle detection apparatus of FIG. 1.
Figure 4:
Figure 5:
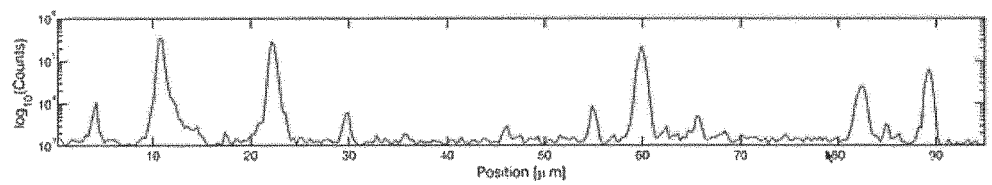

FIGS. 3 to 5 illustrate the scattering intensity as a function of position when an aqueous suspension of dielectric latex nanoparticles are conveyed along the channel path. The dielectric latex nanoparticles have nominal diameters of 19 nm, 35 nm and 51 nm, each of which respectively corresponds to scattering cross-sections of 0.0023 $nm^2$, 0.09 $nm^2$ and 0.86 $nm^2$ for a wavelength of 670 nm.

FIG. 3 is an exemplary raw image of the latex nanoparticles with an exposure time of 1 ms, while FIG. 4 depicts the same image in logarithmic false colour. FIG. 5 illustrates a semi-logarithmic plot of the sum scattering intensity as a function of position. It can be seen from FIGS. 3 and 5 that the particle detection apparatus 30 is capable of detecting the dielectric latex nanoparticles with nominal diameters of 19 nm, 35 nm and 51 nm. In addition the particle detection apparatus 30 enables measurement of the scattering intensity and tracking of each particle's motion through detection of the scattered light.

Such measurement of the scattering intensity of each detected particle and such tracking of each particle's motion not only provides information about each detected particle, but also permits the study of the thermal diffusion and thereby the hydrodynamic behaviour of each particle.

Figure 6:
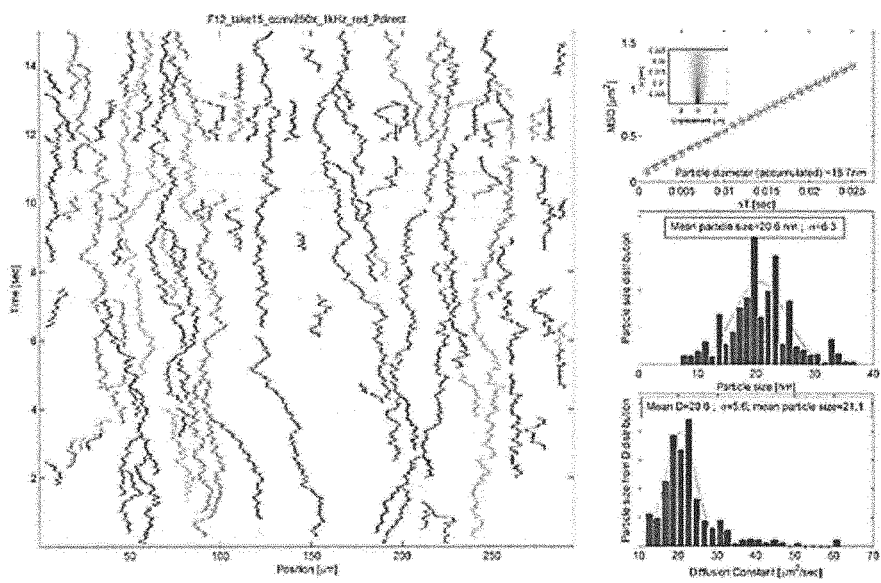
FIG. 6 illustrates the tracking of the positions of single cowpea chlorotic mottle viruses with time using the particle detection apparatus of FIG. 1.

FIG. 6 illustrates the tracking of the positions of single cowpea chlorotic mottle viruses (CCMV) with time using the particle detection apparatus 30. By using the particle detection apparatus 30 to track the position of each detected particle with time, their Brownian motion may be analysed to yield the diffusion constant of each detected particle and hence its size via the Einstein-Stokes equation, as later discussed in this specification. It can be seen from FIG. 6 that the particle detection apparatus 30 is capable of tracking single CCMW with sizes in the range of 20 nm.

Figure 7:
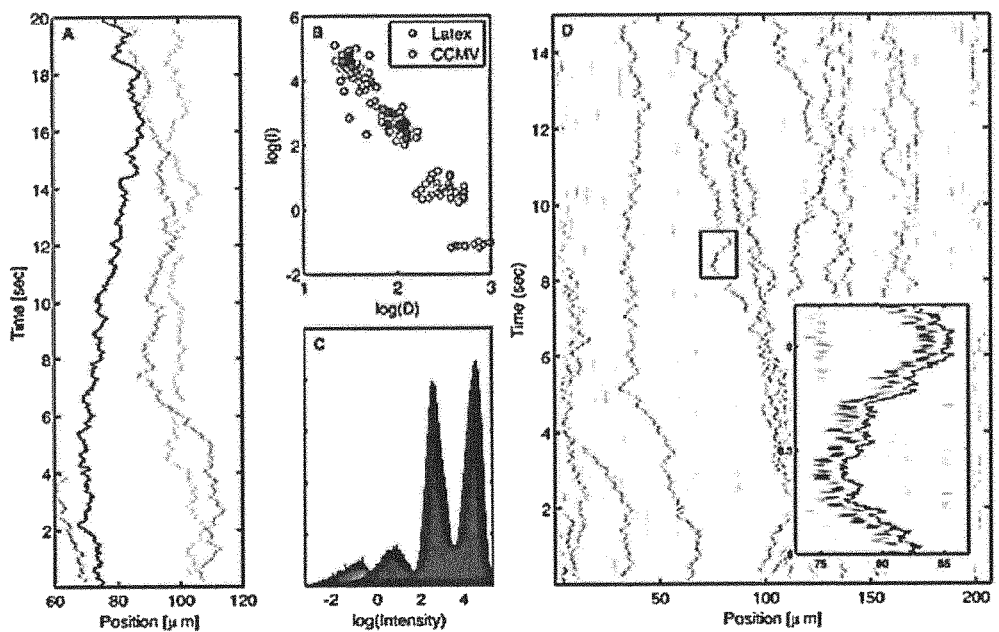
FIG. 7 illustrates the tracking of the positions of dielectric latex nanoparticles and single cowpea chlorotic mottle viruses with time using the particle detection apparatus of FIG. 1.

FIG. 7 illustrates the tracking of the positions of the above dielectric latex nanoparticles and 26 nm single cowpea chlorotic mottle viruses (CCMV) with time using the particle detection apparatus 30.

FIG. 7 includes a plot of the average detected scattering intensity as a function of the extracted diffusion constants for the above dielectric latex particles and 26 nm single CCMV, and a histogram of the logarithm of the detected scattering intensities for the tracked particles. It can be seen from the plot and histogram of FIG. 7, as indicated by reference numerals 42,44,46,50,52,54, that the different dielectric latex nanoparticles with different nominal diameters exhibits significantly different scattering intensities from each other. The particle detection is therefore capable of distinguishing between the different dielectric latex nanoparticles with different nominal diameters based on their different scattering cross-sections.

Moreover it can be seem from the histogram of FIG. 7 that the single CCMV due to their lower index contrast exhibit a lower scattering intensity 56 than that 50,52,54 of the dielectric latex nanoparticles, and so the particle detection apparatus 30 is capable of distinguishing between the dielectric latex nanoparticles and the single CCMV.

Furthermore measurement of the scattering intensity and the Einstein-Stokes diffusion constant of each detected particle allows an aggregate of particles to be distinguished from a single larger particle even if they both exhibit similar scattering intensities.

Each detected particle's diffusion constant and size is obtained by:
- obtaining a displacement histogram for each time interval;
- verifying that the displacement histogram is Gaussian;
- calculate a corresponding mean square displacement (MSD) using the variance of the displacement histogram;
- calculating the diffusion constant as half of the fit to the slope of the MSD against the time interval for small intervals;
- calculating the hydrodynamic diameter of each detected particle using the Einstein-Stokes equation.

The Einstein-Stokes equation for water at room temperature is:

$$\text{Hydrodynamic diameter}(\mu m) = \frac{4.11}{6 \cdot \pi \cdot D}$$

where D is the diffusion constant.

Figure 8:
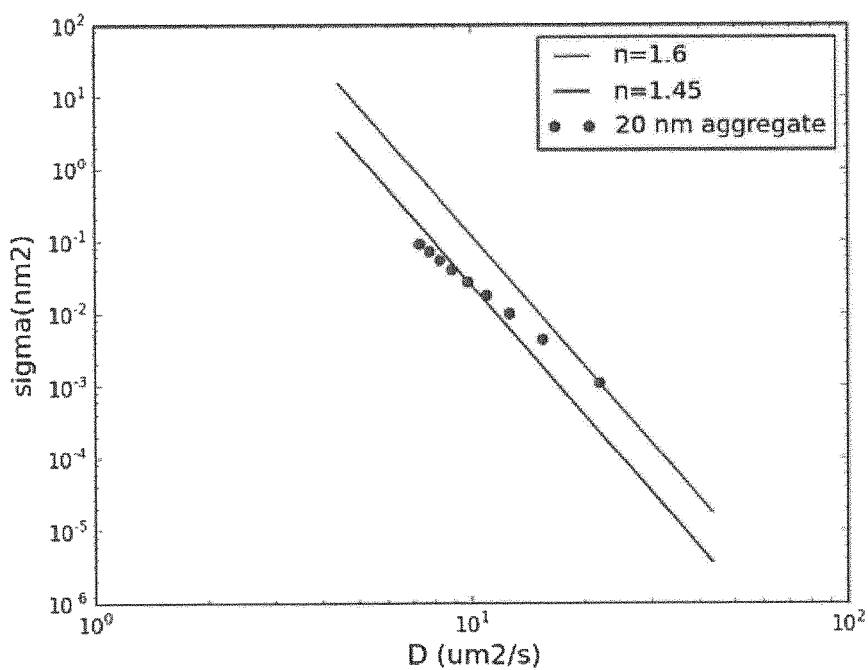
FIG. 8 illustrates a theoretical comparison of scattering cross-section versus diffusion constant for spherical particles of refractive indices and for aggregates of spherical particles.

FIG. 8 illustrates a theoretical comparison of scattering cross-section versus diffusion constant for spherical particles of different refractive indices and for particle aggregates.

The circular dots 58 in FIG. 8 represent a theoretical model of the scattering cross-section versus diffusion constant of aggregates of multiple 20 nm latex nanoparticles. The upper straight line 60 represents a theoretical model of scattering cross-section versus diffusion constant for single full spherical latex particles of different sizes and a refractive index of 1.65. The lower straight line 62 represents a theoretical model of scattering cross-section versus diffusion constant for single full spherical protein particles of different sizes and a refractive index of 1.4.

It can be seen from FIG. 8 that the scattering intensity from aggregates of multiple 20 nm latex nanoparticles exhibits a scaling behaviour with diffusion constant that is different from the scaling behaviours of the full spherical particles of different sizes. Thus, this difference in scaling behaviours allows an aggregate of particles to be distinguished from a single larger particle even if they both exhibit similar scattering intensities.

The configuration of the monitoring device 36 to detect scattered light permits the use of metallic, semiconductor or organic contrast agents to enhance the polarizability of each particle and thereby enhance the detection sensitivity of the particle detection apparatus 30.

FIG. 9 illustrates the tracking of 20 nm to 50 nm latex particles using the particle detection apparatus 30. It can be seen from FIG. 9 that the scattering intensity 64 is brighter than the fluorescence intensity 66. By using the particle detection apparatus 30 to track the position of each detected particle with time, it is evident from FIG. 10 that the scattering intensity remains unchanged while FIG. 11 shows that the fluorescence intensity diminishes with time due to stepwise photo-bleaching. Thus, the use of the particle detection apparatus 30 to detect both scattered and fluorescent light permits simultaneous measurement of the scattering and fluorescence in order to utilise the resultant stepwise photo-bleaching to count the number of fluorophores.

In addition the configuration of the monitoring device 36 to detect both scattered and fluorescent light permits simultaneous measurement of the scattering and fluorescence in order to measure an emission spectrum of each particle. This permits identification of each particle on the basis of its spectral features.

Measurement of the scattering intensity of the scattered light permits the study of particle interaction. For example, measurement of the scattering intensity of the scattered light permits the study of particle binding and unbinding events through detection of quadratic changes in the scattering intensity, the spectral response or the diffusion constant of each particle.

Optionally the monitoring device 36 may be configured to measure the spectrum of the scattered light and/or the distribution of the scattered light over a plurality of directions.

The thermal diffusion of small particles in a liquid is inversely proportional to its size and can reach tens of square micrometers per second for a 10-nanometer spherical particle in water, thus limiting the available detection period to the duration in which the particle spends in an imaging focal place.

On the other hand the configuration of the particle detection apparatus 30 of FIG. 1 allows the particles in the channel path to stay illuminated by the guided light and thereby remain in the imaging plane and not diffuse out of focus. Keeping the particles in the illumination plane of the guide light not only obviates the need for immobilisation of particles in a restricted volume, such as that performed in cryogenic electron microscopy, and thereby results in a less complex and cheaper particle detection apparatus 30, but also provides a prolonged detection period that permits enhanced real-time tracking of each particle and increases the obtainable amount of information about each particle.

In contrast to scattered light detection, in fluorescent microscopy, the speed is limited by the fluorescence emission rate, and the available detection period is truncated by photo-bleaching of the fluorescent light.

The improved detection capabilities of the particle detection apparatus 30 of the invention as set out above not only obviates the need for a specialised monitoring device 36 to detect each particle and thereby permits use of simpler and cheaper monitoring devices, such as an optical microscope, various kinds of photo-detectors, line CCD detectors or a smartphone camera, but also permits detection of each particle under ambient conditions, instead of specific conditions as required by cryogenic electron microscopy.

It is envisaged that, in other embodiments of the invention, the particle detection apparatus 30 may include a driving mechanism for driving each particle to flow along the channel path. In one example of such a driving mechanism, electrodes may be incorporated into the channel 32 to permit use of an electrophoretic force to steer each particle along the channel path.

In another example of such a driving mechanism, the driving mechanism may be external to the channel 32 and may be configured to generate an electric field so as to provide an electrophoretic force to steer each particle along the channel path. Such a driving mechanism may be in the form of a capillary electrophoretic setup. This thereby permits the combination of capillary electrophoresis with the use of the particle detection apparatus 30 to track the motion of each particle.

Figure 17:
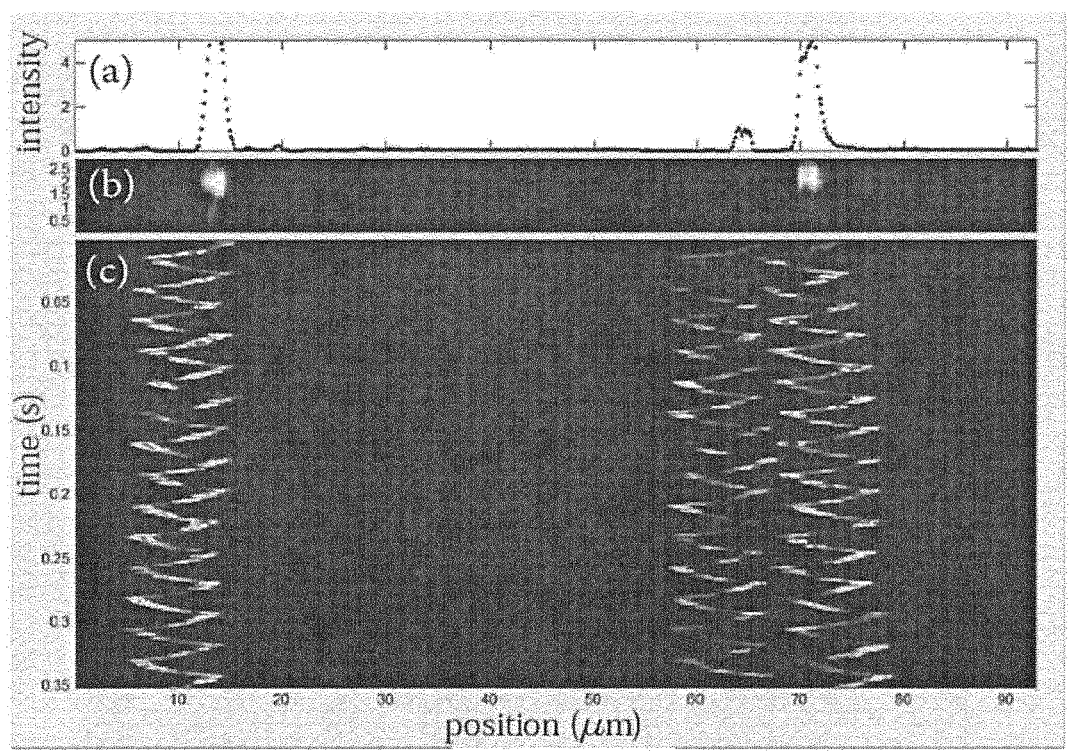
FIG. 17 illustrates the use of the particle detection apparatus of FIG. 1 to track gold nanoparticles that are electrophoretically actuated inside the optical fibre of FIG. 2.

FIG. 17 shows (a) the scattered intensity of three individual 60 nm gold nanoparticles that are electrophoretically actuated inside the optical fibre 38 when measured under the same settings of FIG. 2, (b) the false-colour images of the same three individual 60 nm gold nanoparticles that are electrophoretically actuated inside the optical fibre 38 when measured under the same settings of FIG. 2, and (c) the manipulation of the position of these nanoparticles using an external spatially-uniform temporally alternating electric field.

The zig-zag tracks in FIG. 17(c) depict the position of these particles as a function of time recorded at 1 kHz. This result clearly shows that the capability of the particle detection apparatus 30 to track the motion of the gold nanoparticles beneficially provides active feedback that permits the remote manipulation of the gold nanoparticles in a manner that is strong and fast enough to overcome their thermal Brownian motion.

The combination of capillary electrophoresis with the use of the particle detection apparatus 30 to track the motion of each particle may be, for example, applied to the study of the charging dynamics of proteins at a single-particle level in biologically relevant environments.

In other embodiments of the invention, it is envisaged that the particle detection apparatus may include:
  a plurality of channels, each channel including an inlet and at least one channel wall, each inlet permitting light to be introduced into the respective channel, the or each channel wall being arranged to define a respective channel path through which light may propagate;
  a plurality of light sources, the plurality of light sources being configured to introduce light into the channel via the inlet; and/or
  a plurality of monitoring devices, the plurality of monitoring devices being configured to detect scattered light that is created by the illumination of the or each particle by the guided light and that leaves the channel by passing through the or each channel wall.

When the particle detection apparatus includes a plurality of channels, the monitoring device may be configured to simultaneously detect scattered light that is created by the illumination of the or each particle by the guided light and that leaves each channel by passing through the or each corresponding channel wall.

When the particle detection apparatus includes a plurality of light sources, the plurality of light sources may be configured to simultaneously introduce light into the channel via the inlet.

When the particle detection apparatus includes a plurality of monitoring devices, the plurality of monitoring devices may be configured to simultaneously detect scattered light that is created by the illumination of the or each particle by the guided light and that leaves the channel by passing through the or each channel wall.

Optionally the channel may be formed in an exemplary measuring cell, details of which are set out as follows.

The measuring cell is configured as an optical waveguide for guiding a light beam, said waveguide comprising a core having a refractive index $n_K$, which extends along a longitudinal axis of said waveguide, has a cross-sectional area $A_K$ of less than 80 μm² in a cross section perpendicular to the longitudinal axis, and which is surrounded by a cladding having a smaller refractive index than $n_K$, wherein said cavity forms a channel, extending along the longitudinal axis, being formed inside of or in contact with said core, and having at least one open end with an opening area $A_H$ of less than 0.2 μm².

The channel is formed in an optical fibre, e.g. in a step-index or gradient-index fibre or in another waveguide structure, for instance in a semiconductor microchip manufactured by etching and deposition processes. The light conduction of the optical waveguide is achieved by way of different refractive indices of core and cladding.

The hollow channel serves to receive a fluid medium which contains the sample particles to be analyzed. The fluid medium is here enclosed in the hollow channel or it is guided through the hollow channel by flowing therethrough. The sample particles contained therein can move along the longitudinal axis of the hollow channel, but they are limited in their motion in the directions perpendicular thereto by the width dimension of the channel. In this respect the width dimension of the channel spatially limits the path of movement of the sample particles in lateral direction to a certain degree.

For this purpose the hollow channel is restricted to a width which is defined by an opening area of less than 0.2 μm². In a channel with a circular cross-section this corresponds to a diameter of less than 500 nm. The depth of focus of simple optical microscopes is enough for detecting sample particles within that range. Optionally, however, the hollow channel is even smaller; it has e.g. a diameter in the range of 20 nm to 500 nm, optionally in the range of 50 nm to 300 nm if it is circular in a cross section perpendicular to the longitudinal axis.

The spatial inclusion of the light for an excitation radiation coupled at the front side into the core is all the more pronounced and the light intensity guided in the core is the higher the smaller the cross-sectional area of the core is. A small cross-sectional area of the core facilitates the implementation of a single-mode light conduction also in the case of a shortwave excitation radiation and in the case of a great refractive-index difference between core and cladding. This helps to increase the radiation energy penetrating into the hollow channel and thereby to improve the illumination of the channel. For this purpose the core has a cross-sectional area $A_K$ of less than 80 µm² in a cross section perpendicular to the longitudinal axis. In a core having a circular cross-section this corresponds to a diameter of less than 10 µm. Optionally, however, the core diameter is even smaller; for instance, it has a diameter less than 3 µm if it is circular in a cross section perpendicular to the longitudinal axis. A core diameter of less than 1 µm is not preferred from a practical point of view.

The channel extends within the optical waveguide along the longitudinal axis inside of or in contact with the core. It shares a contact surface with the core. Viewed in a cross section perpendicular to the longitudinal axis (for the sake of simplicity, also briefly called "radial cross-section" hereinafter without the intention to restrict the cross section to the circular shape), the channel extends either directly next to or in contact with the core, or it extends partly or, optionally, fully within the core. At any rate, the hollow channel is defined at least partly, optionally completely, by core material.

The excitation radiation is guided via the core/cladding structure of the optical waveguide along the longitudinal axis and in the hollow channel along a measurement section. Under ray-optical aspects the light conduction is based on total reflection on the condition $n_K > n_M$ (refractive indices at the wavelength of the D line of the sodium vapor lamp). The light guided in the core can here penetrate into the channel and "illuminate" the hollow channel. This light intensity transmission from the core into the hollow channel is not limited to points or locations, but takes place over quite a long section, e.g. along the whole contact surface between core and channel. The light that has penetrated into the channel can thus serve as radiation for exciting scattering or other states of the sample particles existing within the channel, namely over a rather large section, which also permits the monitoring of the movement of the sample particles over a rather long section. The restricted opening width of the hollow channel prevents sample particles from migrating out of the excitation light field.

It is advantageous for an efficient illumination of the sample particles when the intensity distribution within the channel is as great as possible and is homogeneous both in radial and in axial direction. The proportion of the radiation intensity arriving at the channel can serve as a measure of the suitability of the measuring cell design. In this respect the ratio of the intensity minimum in the channel and the maximum intensity in the core is regarded as a measured value. This measured value should be at least 1%, optionally it is 30% or more.

As is known, the number of the light propagation modes in a step-index type optical waveguide depends for a given wavelength substantially on the refractive-index difference between core and cladding and on the core diameter. With respect to a reproducible transfer of guided excitation light into the hollow channel, preference is given to the measuring cell in which the difference between the refractive indices of the core and the cladding, the cross-sectional area of the core and the wavelength of the guided light beam are coordinated such that the fundamental mode of the light beam and not more than 20 further modes may be propagated.

In the case of multispectral excitation radiation, it is advantageous when this condition for the light conduction is fulfilled for the shortest wavelength of the spectrum.

Particularly preferred is per se the measuring cell in which only one single mode, the fundamental mode, is formed, as is the case with so-called single-mode fibres. Here, the guided light intensity is solely transmitted by the fundamental mode, which facilitates the transfer of a light intensity as high as possible into the channel. With the configuration of several modes, the light intensity is distributed over these modes, which on the one hand leads to a low intensity maximum in the core and in the hollow channel. On the other hand, the energy distribution over individual modes is difficult to determine, so that in the case of a multimodal excitation radiation the real intensity distribution in the cavity can be defined less accurately than in the case of a single-mode radiation, which makes the evaluation of the scattered radiation more difficult. The smaller the core (the core diameter), the less light modes are possible under otherwise identical conditions. Therefore, it is true that the single modedness of the light transmission can be ensured in principle in that the size of the core (the core diameter) is set to be sufficiently small. However, a small core size also entails increased manufacturing and adjusting efforts. The smaller the core, the more complicated is the transmission of light into said core. In practice, it is moreover difficult to exactly select the predetermined core diameter and to maintain it over the whole length of the measuring cell. Therefore, on the other hand, a core diameter that is as large as possible would be optimal, in the case of which the single modedness of the light transmission is just barely ensured. Moreover, the channel changes the boundary conditions (boundary conditions regarding the Maxwell equations) underlying the creation of the light modes, so that especially in the case of a near cut-off design with respect to the single-mode light propagation (near the so-called cut-off wavelength) even higher modes may easily be formed. Therefore, apart from the fundamental mode, a certain number of higher modes is considered to be acceptable as long as this number does not exceed 20 modes.

A measuring cell in which core and cladding are composed of highly siliceous glass has turned out to be useful.

"Highly siliceous glass" stands for an optically transparent glass having a $SiO_2$ content that is at least 60% by wt.

In this connection preference is given to a measuring cell in which the core consists of quartz glass which is doped with germanium oxide, and that the cladding consists of quartz glass, which is not doped or which is doped with a component—in particular with fluorine —capable of decreasing the refractive index of quartz glass.

Quartz glass is substantially transparent over a wide wavelength range between about 150 nm and 3000 nm. Hence, the measuring cell allows an excitation radiation with wavelengths in the range from UV to infrared, with a small scattering contribution by the walls of the measuring cell itself. Moreover, the material quartz glass helps to implement hollow channels of a particularly small opening cross-section of for instance less than 100 nm owing to a relatively great temperature interval in which hot formation can be carried out.

Germanium oxide brings about an increase in the refractive index of quartz glass. It has been found that the light intensity guided in the core and thus also the intensity penetrating into the hollow channel is the higher, the greater the refractive index difference between core and cladding is. When the core is doped with germanium oxide and the cladding is simultaneously doped with fluorine, a particularly great refractive-index difference can be established at the core/cladding boundary. This difference is optionally at least $8 \times 10^{-3}$.

Doping the core glass with germanium oxide has a drawback in that germanium may evaporate during high temperature process steps, thereby changing the radial profile of the refractive index. Therefore, the core may consist of undoped quartz glass, and the cladding consists of quartz glass having a refractive index $n_c$, said quartz glass is doped with a component—in particular with fluorine—capable of decreasing the refractive index of quartz glass.

Undoped quartz glass has high optical transmittance and a viscosity higher than doped quartz glass. A high viscosity of the core glass facilitates maintenance of even very small channels inside the core region compared to core glasses with lower viscosity.

It has been found that both a small core diameter and a large difference in refractive contribute to a high intensity of radiation penetrating from core into the channel. In view of that it is advantageous if the core glass is made of undoped quartz glass, and the difference $n_k-n_c$ is at least $16 \times 10^{-3}$, optionally at least $20 \times 10^{-3}$.

It has turned out to be useful when the core and the cladding are made of massive, solid material.

Both core and cladding consist of solid and massive bulk material. Both core and cladding exhibit a nominally homogeneous refractive-index profile in radial cross-section. Local changes in the refractive index due to high temperatures and diffusion processes during the manufacturing process can hardly be prevented. The cladding, however, is without an internal boundary, such as e.g. a further core or a further channel. Likewise, apart from the contact area with the single hollow channel and with the single cladding, the core has no further boundaries. In the absence of boundaries the measuring cell is substantially free of boundary-related scattering; specifically, it has a particularly scatter-free cladding.

Moreover, the effect of so-called mode coupling is avoided, by which energy of a mode is coupled into another mode. This effect may occur when different light-guiding regions are present. Mode coupling has the effect that the energy of the light is periodically exchanged between the different light-guiding regions. This, however, has the effect that the scattering rate along the longitudinal axis of the optical waveguide is varying. Thus, the sample particle would scatter to different degrees axially, depending on the various positions of the fibre, as the light field is periodically varying. This effect could possibly also occur if the hollow channel is not formed inside the core, but away from it. Such a mode coupling may be entirely excluded, so that the intensity of the light (with the exception of the (negligible) attenuation) is axially independent.

It has also turned out to be advantageous when in a cross-section perpendicular to the longitudinal axis, the core is circular having a diameter of less than 10 µm and a core center point which is located inside a respective cross-sectional area of the hollow channel. The hollow channel is optionally provided at a position at which the conditions for the penetration of light out of the core are optimal. Ideally, this position is located in the core center point. The channel, however, can also extend laterally therefrom. In the simplest case of the measuring cell, the core, cladding and hollow channel extend coaxially relative to one another in the optical waveguide. Hollow channel and core are here circular in radial cross-section and concentric relative to each other. The rotation symmetry of the measuring cell is of advantage during use insofar as the measuring conditions and measuring results are independent of the spatial orientation thereof inside the measuring equipment. The core diameter is optionally small and is less than 10 µm, optionally less than 3 µm. The advantages of a small core diameter have been explained further above in connection with its small radial cross-section.

It is advantageous when, on the one hand, high radiation energy is guided in the core, which radiation energy, on the other hand, can penetrate into the channel as efficiently as possible. In this respect preference is given to the measuring cell in which the channel extends entirely inside the core, wherein in a cross section perpendicular to the longitudinal axis, the core has a cross-sectional area $A_K$ and the channel has a cross-sectional area $A_H$, wherein the ratio $A_K/A_H$ is greater than 4, optionally greater than 20.

In this case the hollow channel viewed in radial cross-section extends entirely within the core. It is surrounded over its length by core material, so that the radiation energy guided in the core can efficiently penetrate into the hollow channel. In this case, however, the opening area of the hollow channel (viewed in radial cross-section) is completely at the expense of the cross-sectional area of the core. To be able to provide a sufficiently high radiation energy inside the core, the lateral dimensions of the channel (e.g. its inner diameter) have optionally to be adjusted such that the remaining cross-sectional area of the core is still greater at least by the factor 4, optionally by the factor 20, than the opening area of the hollow channel.

The optical waveguide is here optionally configured as a step-index fibre with a channel, wherein the channel has an opening width which is smaller than the wavelength of a light beam to be guided in the optical waveguide.

In an optional configuration of the measuring cell, the optical waveguide is configured as an optical fibre with a circular cross-section, wherein the cladding has an outer diameter in the range of 150 µm to 300 µm.

A fibre of this thickness is on the one hand still flexible and thus less prone to fracture than a rigid fibre of a greater thickness. On the other hand, its thickness is greater than the optical single-mode standard fibres, so that it can be handled more easily. The cladding can additionally be provided with a protective covering.

The essential advantages of the measuring cell are:
1. spatial inclusion of the sample material;
2. low background signal;
3. possibility of measuring very small particles/molecules; and
4. easy integration of the measuring equipment into existing, commercially available and wide-spread measuring instruments and thus small acquisition costs together with moderate production costs of the optical waveguide.

The measuring cell is obtained from the preform by elongation, wherein the measuring cell is present in the form of an optical fibre with light-conducting hollow channel. The hollow channel extends in radial cross-section entirely within the core of the optical fibre. It is surrounded over its length by core material, resulting in an effective penetration of radiation energy into the channel, with the radiation energy being guided in the core. To be able to provide a sufficiently great amount of radiation energy in the core, the lateral dimensions of the channel (e.g. its inner diameter) must optionally be set such that the remaining cross-sectional area of the core is still by at least the factor 4, optionally by the factor 20, greater than the cross-sectional area of the channel.

In the simplest case, this ratio in the preform from which the optical fibre is drawn true to scale is already predetermined.

Details of a further exemplary measuring cell is set out as follows, with reference to FIGS. 12 to 16.

The exemplary measuring cell is used in the form of an optical hollow fibre 1 with a core 2, a cladding 3, and a light-guiding channel 4.

Due to the core/cladding structure of the fibre an introduced laser light is guided in the fibre core 2 and reaches—also within the channel 4—an intensity that is sufficient for optically analyzing sample volumes introduced into this cavity. This is the case whenever the width of the hollow channel 4 is in the order of magnitude of the wavelength of the guided light or is smaller. Thus, the light conduction of the hollow fibre 1 makes it possible to illuminate the hollow channel volume over the whole length in a quasi-uniform manner. As a result, the region from which light can be detected for the microscopic analysis is not limited to a spot region.

Figure 12:
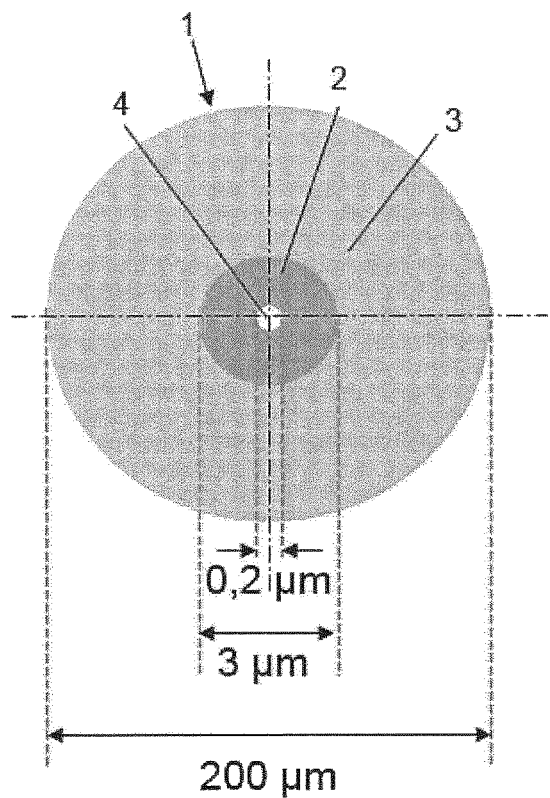
FIG. 12 shows a measuring cell in the form of an optical fibre with a hollow channel in a top view on a front side of the fibre.

FIG. 12 schematically shows the measuring cell in the form of an optical fibre 1 with the light-guiding hollow channel 4 in a top view on the front side of the fibre. The core 2 consists of germanium oxide-doped quartz glass and has an outer diameter of 3 μm. The cladding 3 adjoining the core 2 consists of undoped quartz glass and has an outer diameter of 200 μm. The channel 4 has a diameter of 200 nm. The difference between the refractive indices of the quartz glasses of core 2 and cladding 3 is 0.008. The channel 4, the core 2, and the cladding 3 extend coaxially about the longitudinal axis 9 and are concentric to one another in the plane of representation of FIG. 12. Apart from the hollow channel 4, neither the core 2 nor the cladding 3 exhibit other structural irregularities or inhomogeneities that might lead to scattering. A few centimeters of the fibre length are sufficient for a respective measurement.

Hence, the optical fibre 1 consists of quartz glass and, in comparison with other optical materials, such as multicomponent glasses or optical plastics, it exhibits low attenuation for light from the ultraviolet up and far into the infrared wavelength range and thus also exhibits an excellent light scattering. This property reduces the scattering background in the measurement to a minimum and allows a good signal-to-noise ratio. This is particularly important in the case of very small sample particles because the scattering signal of the sample particles correlates in an over-linearly reciprocal manner with the particle diameter. The described reduction of the scattering background is therefore positively noticed particularly in the analysis of especially small sample particles 5, as are e.g. found in biological processes and which could so far not be analyzed with this method because of their small dimension. Viruses should here be mentioned by way of example.

For the same reason it is moreover possible in many cases to dispense with the additional marking of the sample particles to be analyzed with fluorescent substances. The amount of the intensity of the scattered light is not physically limited in contrast to the saturation behavior of the fluorescence of every fluorescent molecule, but depends particularly on the local intensity of the excitation light. When the excitation intensity can be increased, the whole intensity of the scattered light is increasing. Sufficiently high scattering results can thereby also be achieved within short time intervals. This makes it possible to directly track biochemical processes, including possible intermediate steps, and thereby to measure the properties which can be analyzed with this method.

Figure 13:
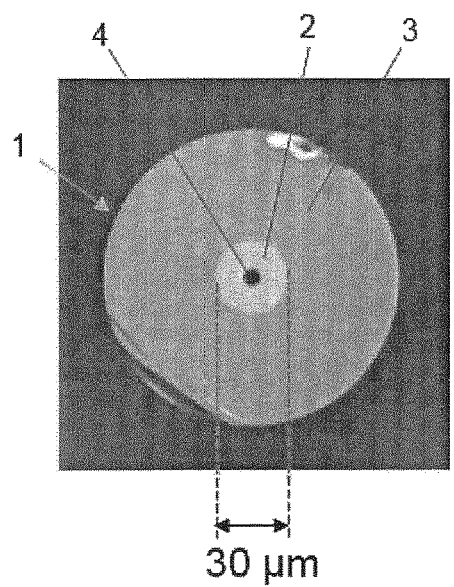
FIG. 13 is a micrograph showing a fracture surface of a thin tube from which the measuring cell is produced (FIG. 6; reference numeral 89)

FIG. 13 is a micrograph of a fracture surface in an intermediate product from which the optical fibre is obtained with core 2, cladding 3 and the light-guiding hollow channel 4 by true-to-scale elongation after a further production step of increasing the amount of cladding material. The optical fibre 1 with the hollow channel 4 has to fulfill one or more of the following tasks:

- reception of the fluid with one or more sample particles 5.
- restriction of the space in which the sample particles 5 can move. The sample particles 5 are here substantially restricted to a one-dimensional movement in the direction of the longitudinal axis 9.
- transmission of the excitation light to the sample particles 5. It is the aim to achieve a light intensity which is as high as possible within the whole channel 4, if possible.
- especially in the case where elastic light scattering is to be detected, the minimization of the background scattering level is important (by use of quartz glass in comparison with other materials for the optical fibre).

The constructional design of the optical fibre 1 is chosen such that the light intensity within the hollow channel 4 is as high as possible. For example,

- the optical fibre comprises at least a light-guiding fibre core 2, a cladding 3, and a hollow channel 4;
- the hollow channel 4 is located in or directly on the fibre core 2, so that a proportion of the excitation light, which is supplied through the fibre core 2, penetrates into the hollow channel 4. Optionally, the hollow channel 4 is completely positioned with the fibre core 2;
- the optical fibre 1 is a single-mode fibre or a fibre with the fundamental mode and otherwise with just a small number of modes (optionally with the fundamental mode and less than 20 secondary modes);
- the hollow channel 4 is a cavity which is open at both sides or is closed (in the last-mentioned case, the sample medium is enclosed, for instance in that the ends of the hollow fibre are spliced with other optical fibres without hollow channel);
- the hollow channel 5, viewed in radial cross-section, has a circular shape and a diameter which is in the order of magnitude of the wavelength of the guided light or less;
- the optical fibre 1 has a high numerical aperture and thus a core diameter which is as small as possible, so that the light intensity in the hollow channel 4 is maximized; and
- the optical fibre 1 consists of doped and/or undoped quartz glass to prevent a strong scattering background.

Figure 14:
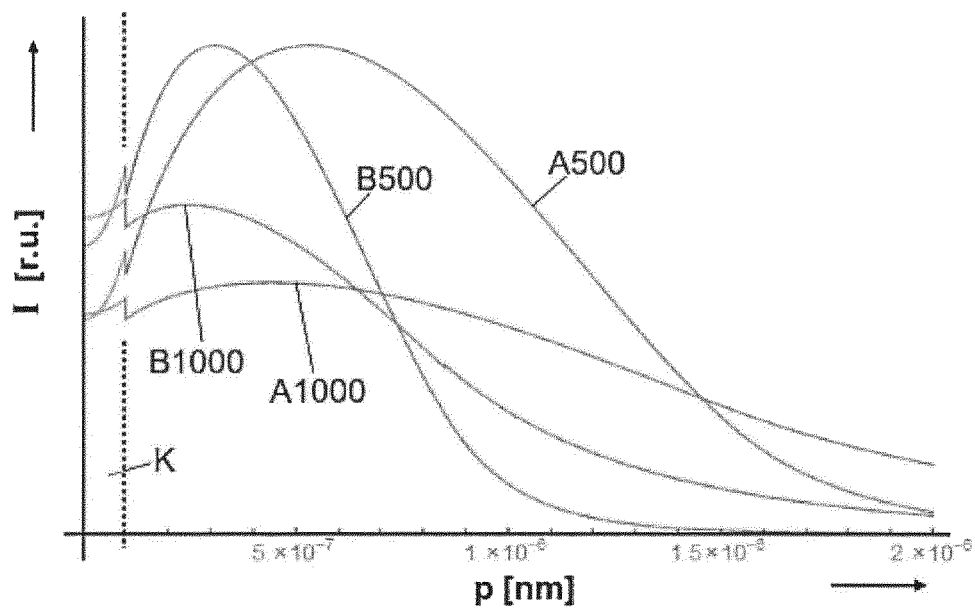
FIG. 14 shows a diagram with radial radiation intensity curves of the guided light in two different examples of the optical fibre and for different wavelengths of the guided light.

FIG. 14 shows results of a simulation regarding the radial intensity profile within the optical fibre 1. On the ordinate of the diagram, the z-component (along the longitudinal fibre axis 9) of the Poynting vector "l" is plotted (in relative units) against the radial position "p" (in nm) starting from the centre of the hollow channel K (p=0). The amount of the Poynting vector corresponds to the intensity of the fundamental mode guided in the fibre in the event that the hollow channel 4 is filled with water (refractive index of water: 1.33).

Curves A500 and A1000 represent the radial intensity profile of a fibre, whereby A500 is simulated for a guided light having a wavelength of 500 nm, and A1000 is simulated for a guided light having a wavelength of 1000 nm. In this case, the refractive index difference between cladding 2 and core 3 is 0.008 (typical order of magnitude of standard single-mode fibres); the core has a diameter of 3 μm.

In comparison with an undisturbed core, one obtains a different intensity curve of the fundamental mode in a core 3 having a central bore 4 (which is 200 nm in this case). The intensity maximum is not located in the fibre center, but approximately in the center between inner wall of the cladding and wall of the hollow channel. It can be seen that within the water-filled hollow channel K the intensity drops only slightly and is even at the minimum in the same order of magnitude of the amplitude of the total curve.

The ratio of the intensity minimum in the hollow channel K (in the centre) and the maximum intensity in the core is about 50% in this particular design.

By comparison, curves B500 and B1000 show the intensity distribution of the fundamental mode in a fibre with an increased refractive index difference between core and cladding. The core consists of undoped quartz glass and has an outer diameter of 1.7 µm. The cladding consists of quartz glass which is doped with fluorine and has an outer diameter of 200 µm. The hollow channel has a diameter of 200 nm. The difference between the refractive indices of the quartz glasses of core and cladding is here 0.025. Curve B500 is simulated for a guided light having a wavelength of 500 nm. Curve B1000 is simulated for a guided light having a wavelength of 1000 nm.

Particularly on account of the higher refractive index difference compared to curves A500 and A1000, for this measuring cell the total radiation intensity guided in the hollow channel of the total intensity of the radiation inside the core 3 is larger than in the respective B500 and B1000 curves. In case of curve B500, the ratio of the intensity minimum in the hollow channel 4 (in the centre) and the maximum intensity in the core 3 is about 60%.

The comparison between curves A500 and A1000 and curves B500 and B1000 shows that the guided light with higher wavelength (1000 nm) results in a more even radial distribution profile of intensity I in the core region as well as in the channel region K.

Figure 15:
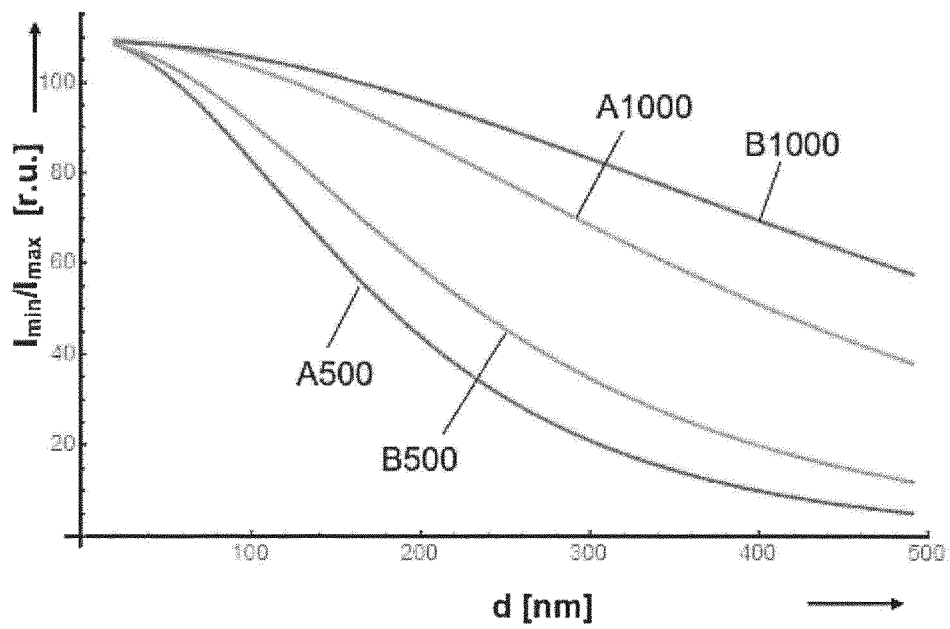
FIG. 15 shows a simulation of the maximum intensity measured in the light-guiding hollow channel in dependence upon the diameter of the hollow channel (Poynting vector)
Figure 16:
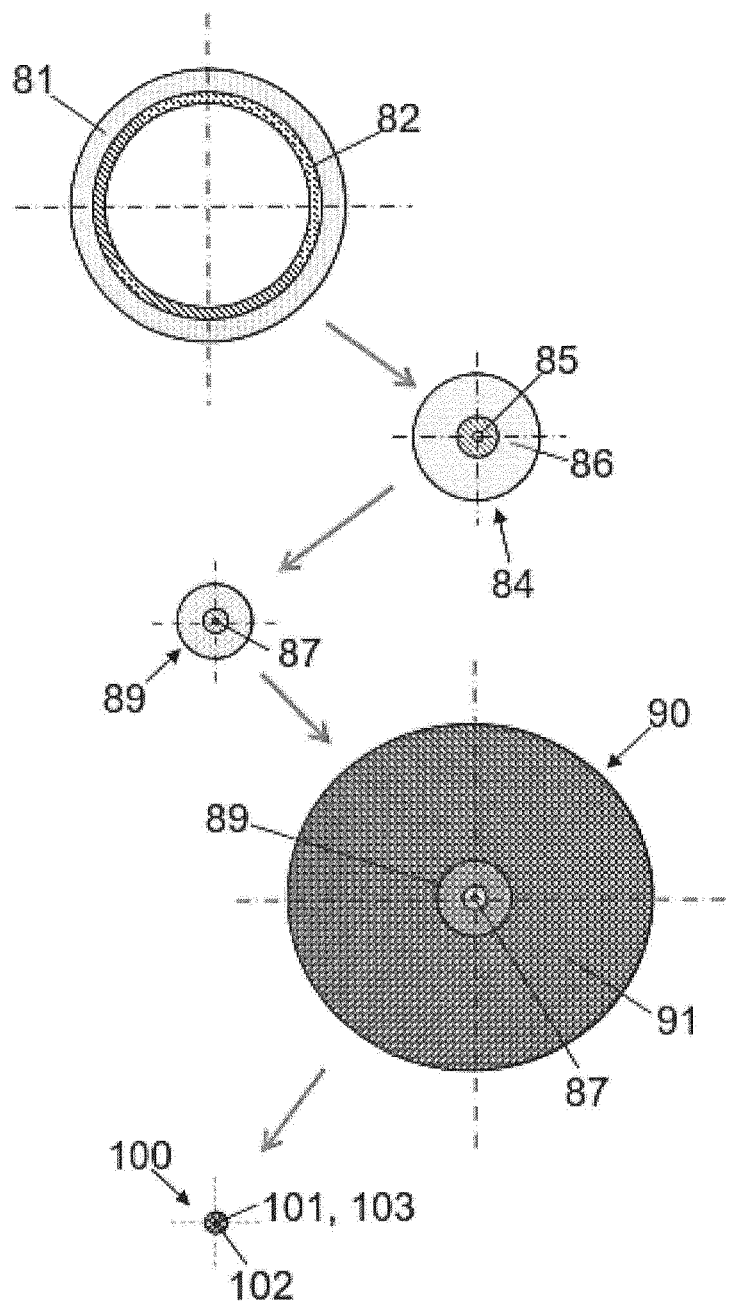
FIG. 16 shows method steps for producing a measuring cell.

The diagram of FIG. 15 illustrates the influence of the inner diameter of the hollow channel on the radiation intensity guided within the hollow channel for two particular wavelengths 500 nm and 1000 nm. As is FIG. 14, curves A500 and A1000 represent the radial intensity profile of a fiber, whereby curve A500 is simulated for a guided light having a wavelength of 500 nm, A1000 is simulated for a guided light having a wavelength of 1000 nm while the refractive index difference between core 3 and cladding 2 is 0.008 and the diameter of the core is 3.0 µm in accordance with curves A500 and A1000 from FIG. 14. Curve B500 is simulated for a guided light having a wavelength of 500 nm, B1000 is simulated for a guided light having a wavelength of 1000 nm each for the case of a refractive index difference of 0.025 and a core diameter of 1.7 µm. On the ordinate of the diagram, the ratio $l_{min}/l_{max}$ (in %) of the minimum of the z-component of the Poynting vector inside the channel 4 and the maximum of the Poynting vector "l" in the core is plotted against the diameter d (in nm; as opening width) of the hole. Here, this ratio represents the amount of decrease of light intensity within the channel.

It is evident from this that the radiation intensity guided in the hollow channel depends on the inner diameter of the hollow channel. The smaller the diameter, the higher the intensity values at the minima inside the hole will become. On the other hand, the smaller the hole, the more difficult it will become to manufacture as well as to work with the device (evidentially also only particles smaller than the hole size are physically capable of entering it). Consequently, a trade-off between required minimal intensity and minimal hole diameter yields a practically favourable hole diameter of 50 nm to 300 nm in diameter.

The optical fiber 1 with hollow channel 4 is drawn from a preform. The production of a preform for a measuring cell with a refractive index difference of the fiber represented by curve A in FIG. 14 shall be explained hereinafter with reference to an example and with reference to FIG. 16 in more detail.

In a first method step, a so-called substrate tube 81 is provided. The substrate tube 81 consists of undoped quartz glass and has an inner diameter of 21 mm and a wall thickness of 2 mm. On the inner wall of the bore of the substrate tube 81, a core layer 82 of germanium-containing quartz glass is deposited on the inside of the substrate tube. The undoped quartz glass will subsequently serve as the cladding material according to the known MCVD method. The germanium content of the core layer 82 is set such as to meet a refractive index difference of 0.008 with respect to the undoped quartz glass of the cladding material. The substrate tube 81 which is thereby coated on the inside is subsequently collapsed to form a quartz glass tube 84, wherein a bore 85 with a diameter of 0.5 mm is maintained. The germanium-containing layer forms a hollow core 86 with an outer diameter of about 3 mm. The outer wall of the quartz glass tube 84 is flame-polished by means of an oxyhydrogen burner. The quartz glass tube 84 cleaned in this way is elongated in a drawing process without any tools to a thin tube 89 having an outer diameter of roughly 2 mm. During the elongation process the inner hole of the quartz glass tube and of the drawn-off tube strand, respectively, is flushed with nitrogen. The inner hole 87 of the thin quartz glass tube 89 obtained thereby has a diameter of about just below 100 µm. The quartz glass tube 89 is overcladded in a further method step with a so-called jacket tube 91 of undoped quartz glass. The thin quartz glass tube 89 is introduced into the bore of the jacket tube, it is coaxially centred therein and fused therewith zone by zone to form a thick-walled tubular preform 90. The tubular preform 90 produced thereby has an outer diameter of roughly 30 mm and in a radial cross-section it shows a concentric arrangement of inner hole 87.

The preform 90 has a single-mode step-index design and a coaxial central bore, in addition. It is drawn into an optical fiber 100 with a light-guiding hollow channel 101. In order to avoid total collapsing, the inner hole 87 is pressurized with nitrogen during the drawing process. The resulting fiber 100 has a nominal diameter of 200 µm. It is formed from a coaxial arrangement of an inner hole 101, a core region 103 of Ge-doped quartz glass and an outer cladding region 102 of undoped quartz glass. The inner hole 101 has a diameter of just below 600 nm, the core region 103 has an outer diameter of just below 3 µm.

Hereinafter, an alternative manufacturing process of a measuring cell shall be described. The manufacturing process involves a deposition step in which a layer of fluorine-doped quartz glass is produced on a support tube by means of a standard POD method (Plasma-assisted Outside Deposition). The support tube consists of undoped synthetic quartz glass. It has an inner diameter of 5 mm and an outer diameter of 40 mm. To this end $SiCl_4$, oxygen and $SF_6$ are supplied to a plasma burner and are converter into $SiO_2$ particles in a burner flame assigned to the plasma burner. Since the plasma burner is reversingly moved along the support tube from one end to the other one, the $SiO_2$ particles are deposited in layers on the outer cylindrical surface of the support tube rotating about its longitudinal axis. It is thereby possible to incorporate high fluorine concentrations of more than 5 wt.-% in the quartz glass network of the fluorine doped quartz glass layer having a thickness of 15 mm.

Following the deposition process a heated etching gas stream of $SF_6$ is introduced into the centre bore of the support tube. The etching gas stream of $SF_6$ is configured such that the support tube is not completely removed, but a layer of undoped silica with a thickness of 15 mm remains. A mechanical treatment of the inner bore of the tubular form (=starter tube) is not needed.

The starter tube produced in this way is subsequently drawn in an elongation process without any tools into a double-walled tube having a core layer of undoped silica and a cladding layer of fluorine-doped quartz glass. To this end an internal pressure which in comparison with the externally applied external pressure is raised by 5 mbar is maintained in the inner bore. This yields a double-walled tube which comprises an inner wall which is smoothed by hot deformation and has a particularly high surface quality and an exact width of the inner bore over the whole length of the tube.

The resulting double-walled tube is further processed in a second POD deposition process for the further deposition of a layer of fluorine-doped quartz glass, as has been described above for the making of the starter tube, resulting in a thick-walled "mother tube".

The mother tube is elongated in order to obtain an optical fiber with a light-guiding hollow channel, as has been explained above with reference to curve B in FIG. 14. Besides the coaxial inner hollow channel the resulting fiber has single-mode step-index design. It has a core of undoped silica and a cladding of fluorine-doped silica. Segments with the desired lengths are produced from the optical fiber obtained in this way, the segments being used as a measuring cell.

The invention claimed is:

1. A particle detection apparatus comprising:
    a channel including an inlet and at least one channel wall, the inlet permitting light to be introduced into the channel, the or each channel wall enclosing a sub-wavelength bore that defines a channel path through which light may propagate;
    a light source configured to introduce light into the channel via the inlet, the channel being shaped to guide the light to propagate along the channel path for illuminating a particle or a plurality of particles located in the channel path; and
    a monitoring device configured to detect scattered light that is created by the illumination of the or each particle by the guided light and that leaves the channel by passing through the or each channel wall.

2. A particle detection apparatus according to claim 1 wherein the inlet is configured as an open inlet.

3. A particle detection apparatus according to claim 2 wherein the open inlet is configured to permit the or each particle to be introduced into the channel.

4. A particle detection apparatus according to claim 1 wherein the inlet is configured as a light incoupling inlet.

5. A particle detection apparatus according to claim 1 wherein the scattered light leaves the channel through the or each channel wall at a non-zero angle to a guided direction of the guided light.

6. A particle detection apparatus according to claim 1 wherein the monitoring device is configured to measure the coherent scattering intensity of the scattered light, the incoherent scattering intensity of the scattered light, the spectrum of the scattered light, the distribution of the scattered light over a plurality of directions and/or the dynamic motion of the or each particle.

7. A particle detection apparatus according to claim 1 wherein the monitoring device is configured to track the or each particle's motion through detection of the scattered light.

8. A particle detection apparatus according to claim 1 wherein the monitoring device is configured to measure an emission spectrum of the or each particle.

9. A particle detection apparatus according to claim 1 wherein the monitoring device is configured to detect fluorescent light that is created by the illumination of the or each particle by the guided light and that leaves the channel by passing through the or each channel wall.

10. A particle detection apparatus according to claim 1 wherein the monitoring device is configured to detect coherently scattered light and/or incoherently scattered light, and optionally detect the spectrum of the coherently scattered light and/or incoherently scattered light, that is created by the illumination of the or each particle by the guided light and that leaves the channel by passing through the or each channel wall.

11. A particle detection apparatus according to claim 10 wherein the monitoring device is configured to track the or each particle's motion through detection of the coherently scattered light and/or incoherently scattered light.

12. A particle detection apparatus according to claim 1 wherein the channel is arranged to convey at least one particle that is smaller than the wavelength of the guided light.

13. A particle detection apparatus according to claim 1 wherein the channel is formed in or as:
    a waveguide;
    a chip-based platform, optionally a lithographically formed chip-based platform; or
    a capillary.

14. A particle detection apparatus according to claim 1 wherein the channel is formed in or as an optical fibre.

15. A particle detection apparatus according to claim 14 wherein the optical fibre is a single-mode optical fibre.

16. A particle detection apparatus according to claim 14 wherein the optical fibre is made from silica or polymer.

17. A particle detection apparatus according to claim 1 wherein the particle detection apparatus includes a driving mechanism for driving the or each particle to flow along the channel path.

18. A particle detection apparatus according to claim 17 wherein the driving mechanism includes electrodes, which are incorporated into the channel and are configured to provide an electrophoretic force to steer the or each particle along the channel path.

19. A particle detection apparatus according to claim 17 wherein the driving mechanism is external to the channel and is configured to generate an electric field so as to provide an electrophoretic force to steer the or each particle along the channel path.

20. A particle detection apparatus according to claim 17 wherein the driving mechanism is configured to drive the or each particle to overcome its or their thermal Brownian motion when driving the or each particle to flow along the channel path.

21. A particle detection apparatus according to claim 1 wherein the monitoring device includes at least one light detector and/or an imaging device configured to process the detected light so as to create an output signal corresponding to the or each particle.

22. A particle detection apparatus according to claim 1 including a plurality of channels, each channel including an inlet and at least one channel wall, each inlet permitting light to be introduced into the respective channel, the or each channel wall being arranged to define a respective channel path through which light may propagate.

23. A particle detection apparatus according to claim 22 wherein the monitoring device is configured to simultaneously detect scattered light that is created by the illumination of the or each particle by the guided light and that leaves each channel by passing through the or each corresponding channel wall.

24. A particle detection apparatus according to claim 1 including a plurality of light sources, the plurality of light sources being configured to introduce light into the channel via the inlet.

25. A particle detection apparatus according to claim 24 wherein the plurality of light sources is configured to simultaneously introduce light into the channel via the inlet.

26. A particle detection apparatus according to claim 1 including a plurality of monitoring devices, the plurality of monitoring devices being configured to detect scattered light that is created by the illumination of the or each particle by the guided light and that leaves the channel by passing through the or each channel wall.

27. A particle detection apparatus according to claim 26 wherein the plurality of monitoring devices is configured to simultaneously detect scattered light that is created by the illumination of the or each particle by the guided light and that leaves the channel by passing through the or each channel wall.

28. A particle detection apparatus according to claim 1 wherein the monitoring device is configured to measure the coherent scattering intensity of the scattered light, the incoherent scattering intensity of the scattered light, the spectrum of the scattered light, the distribution of the scattered light over a plurality of directions and/or the Einstein Stokes diffusion constant of the or each particle.

29. A method of detecting at least one particle, the method comprising the steps of: providing a channel including an inlet and at least one channel wall, the inlet permitting light to be introduced into the channel, the or each channel wall enclosing a sub-wavelength bore that defines a channel path through which light may propagate;

providing a particle or a plurality of particles in the channel path;

introducing light into the channel via the inlet, the channel being shaped to guide the light along the channel path and thereby illuminate the particle or the plurality of particles located in the channel path; and detecting scattered light that is created by the illumination of the or each particle by the guided light and that leaves the channel by passing through the or each channel wall.

* * * * *